United States Patent
Schade

(10) Patent No.: US 12,181,369 B2
(45) Date of Patent: Dec. 31, 2024

(54) METHOD AND DEVICE FOR DETERMINING THE SHAPE OF AN OPTICAL WAVEGUIDE, AND DEVICE FOR PRODUCING TRAINING DATA FOR A NEURAL NETWORK

(71) Applicant: FRAUNHOFER-GESELLSCHAFT ZUR FÖRDERUNG DER ANGEWANDTEN FORSCHUNG E.V., Munich (DE)

(72) Inventor: Wolfgang Schade, Goslar (DE)

(73) Assignee: FRAUNHOFER-GESELLSCHAFT ZUR FÖRDERUNG DER ANGEWANDTEN FORSCHUNG E.V., Munich (DE)

( * ) Notice: Subject to any disclaimer, the term of this patent is extended or adjusted under 35 U.S.C. 154(b) by 231 days.

(21) Appl. No.: 17/694,151

(22) Filed: Mar. 14, 2022

(65) Prior Publication Data
US 2022/0221373 A1    Jul. 14, 2022

Related U.S. Application Data

(63) Continuation-in-part of application No. PCT/EP2019/074389, filed on Sep. 12, 2019.

(51) Int. Cl.
*G01M 11/08* (2006.01)
*A61B 34/20* (2016.01)
(Continued)

(52) U.S. Cl.
CPC .......... *G01M 11/088* (2013.01); *A61B 34/20* (2016.02); *G01B 11/18* (2013.01); *G01L 1/245* (2013.01);
(Continued)

(58) Field of Classification Search
CPC .... G01M 11/088; G01M 11/31; G01M 11/30; A61B 34/20; A61B 2034/2061;
(Continued)

(56) References Cited

U.S. PATENT DOCUMENTS

| 6,256,090 B1 * | 7/2001 | Chen ................. G01V 1/3835 356/73.1 |
| 10,217,237 B1 * | 2/2019 | Goncharov ............... B21F 1/00 |

(Continued)

FOREIGN PATENT DOCUMENTS

| CN | 109186490 A * | 1/2019 | .......... G01B 11/255 |
| WO | WO-2019037071 A1 * | 2/2019 | ............. G01B 11/26 |

OTHER PUBLICATIONS

N. Zeng et al., "Enhancement of the measurement range of FBG sensors in a WDM network: a self-organizing network solution", Sensors and Actuators A: Physical, vol. 118, Issue 2, 2005, pp. 233-237, ISSN 0924-4247 (Year: 2005).*

(Continued)

*Primary Examiner* — Michelle M Iacoletti
*Assistant Examiner* — Noah J. Haney
(74) *Attorney, Agent, or Firm* — Womble Bond Dickinson (US) LLP

(57) ABSTRACT

A method for determining the shape of an optical waveguide (1) having a plurality of fiber Bragg gratings (15) includes the following steps: coupling light (20) of a light source (2) into the optical waveguide (1), coupling the reflected light out of the optical waveguide (1), determining a spectrum (35) of the reflected light by measuring the intensity (I) versus the wavelength ($\lambda$), the spectrum (35) being fed to a self-learning neural network (4) and the shape of the optical waveguide (1) being determined by the neural network. A device for determining the shape of an optical waveguide (1) may be used in a catheter or an endoscope or a biopsy needle (Continued)

or an aerodynamic profiled element. A device for producing training data for a neural network to implement the above is also contemplated.

14 Claims, 4 Drawing Sheets

(51) Int. Cl.
| | |
|---|---|
| *G01B 11/16* | (2006.01) |
| *G01L 1/24* | (2006.01) |
| *G01M 11/00* | (2006.01) |
| *G06N 3/08* | (2023.01) |

(52) U.S. Cl.
CPC .............. *G01L 1/246* (2013.01); *G01M 11/31* (2013.01); *G06N 3/08* (2013.01); *A61B 2034/2061* (2016.02)

(58) Field of Classification Search
CPC .......... G01B 11/18; G06N 3/08; G01L 1/245; G01L 1/246
USPC ....................................................... 356/73.1
See application file for complete search history.

(56) References Cited

U.S. PATENT DOCUMENTS

| | | | |
|---|---|---|---|
| 10,551,170 B2* | 2/2020 | 'T Hooft | A61B 1/009 |
| 10,962,351 B2* | 3/2021 | Roye | G01B 9/02004 |
| 2007/0297714 A1 | 12/2007 | Dua et al. | |
| 2009/0116000 A1* | 5/2009 | Kiddy | G01B 11/18 |
| | | | 356/73.1 |
| 2009/0123111 A1* | 5/2009 | Udd | G01D 5/35303 |
| | | | 385/13 |
| 2009/0285521 A1* | 11/2009 | Kunigami | G01B 11/18 |
| | | | 385/13 |
| 2010/0215311 A1* | 8/2010 | Moore | G01B 11/18 |
| | | | 356/73.1 |
| 2012/0289777 A1* | 11/2012 | Chopra | A61B 5/6852 |
| | | | 382/128 |
| 2017/0095143 A1* | 4/2017 | Sato | G01B 11/18 |
| 2017/0160109 A1 | 6/2017 | Schade et al. | |
| 2019/0170930 A1 | 6/2019 | Schade et al. | |
| 2019/0390985 A1* | 12/2019 | Kwok | G01B 11/24 |

OTHER PUBLICATIONS

Lun et al., "Real-Time Surface Shape Sensing for Soft and Flexible Structures Using Fiber Bragg Gratings," IEEE Robotics and Automation Letters, Apr. 2019, 4(2):1454-1461.

Van Meerbeek et al., "Soft optoelectronic sensory foams with proprioception," Sci. Robot, Nov. 28, 2018, 3:eaau2489, 8 pp.

Waltermann et al., "Fiber-Optical 3D Shape Sensing; in G. Marowsky (ed.), Planar Waveguides and other Confined Geometries: Theory, Technology, Production, and Novel Applications," Springer Series in Optical Sciences 189, Springer New York, 2015, pp. 227-250.

Zeng et al., "Enhancement of the measurement range of FBG sensors in a WDM network: a self-organizing network solution," Sensors and Actuators, 2005, 118(2):233-237.

Zheng et al., "Artificial neural network for the reduction of birefringence-induced errors in fiber shape sensors based on cladding waveguides gratings," Optics Letters, Apr. 2020, 45(7):1726-1729.

* cited by examiner

METHOD AND DEVICE FOR DETERMINING THE SHAPE OF AN OPTICAL WAVEGUIDE, AND DEVICE FOR PRODUCING TRAINING DATA FOR A NEURAL NETWORK

CROSS REFERENCE TO RELATED APPLICATIONS

The present application is a Bypass Continuation-in-Part of International Application No. PCT/EP2019/074389, filed Sep. 12, 2019 and published as WO 2021/047779A1. The contents of the aforementioned application are incorporated by reference in their entirety.

FIELD OF THE INVENTION

The invention relates to a method and a device for determining the shape of an optical waveguide having a plurality of fiber Bragg gratings, comprising the following steps: coupling light of a light source into the optical waveguide, coupling reflected light out of the optical waveguide, determining the spectrum of the reflected light by measuring the intensity versus the wavelength. Methods and devices of this type can be used to detect the shape of an object provided with at least one optical waveguide.

DE 10 2016 214 887 A1 discloses a device and a method of the above mentioned type. This known fiber-optic sensor has an optical waveguide into which fiber Bragg gratings are present. The Bragg gratings are radially spaced apart, i.e. arranged at different distances and/or in different directions from the axis of symmetry of the cross-section of the optical waveguide. When the optical waveguide is deformed, the grating constant of the Bragg gratings is changed due to stretching on the outside of the curvature or compression on the inside of the curvature. In addition, the mode field of the light propagating inside the optical waveguide shifts. This changes the reflection wavelength and/or the intensity of reflected light. The curvature at the location of the Bragg gratings can be determined from these changes in the spectrum.

This known device has the disadvantage that a curvature may not be detected in a longitudinal portion where no Bragg grating is present. In particular, the shape of optical waveguides having a great length may be reconstructed only incompletely under some conditions.

In view of the prior art, it is an object of the invention to provide a device and a method that allows greater accuracy in determining the shape of an optical waveguide and an object attached therewith.

SUMMARY OF THE INVENTION

In one aspect, the invention relates to a method for determining the shape of an optical waveguide having a plurality of fiber Bragg gratings, said method comprising the following steps:
coupling light of a light source into the optical waveguide,
coupling the reflected light out of the optical waveguide,
determining spectrum data of the reflected light by measuring the intensity versus the wavelength,
providing the spectrum data to a self-learning neural network having been preconditioned by training data, and
determining the shape of the optical waveguide by means of this neural network.

BRIEF DESCRIPTION OF THE DRAWINGS

The accompanying figures, where like reference numerals refer to identical or functionally similar elements throughout the separate views, which are not true to scale, and which, together with the detailed description below, are incorporated in and form part of the specification, serve to illustrate further various embodiments and to explain various principles and advantages all in accordance with the devices. Advantages of embodiments of the devices will be apparent from the following detailed description of the exemplary embodiments thereof, which description should be considered in conjunction with the accompanying drawings in which.

DETAILED DESCRIPTION

Figure 1A:
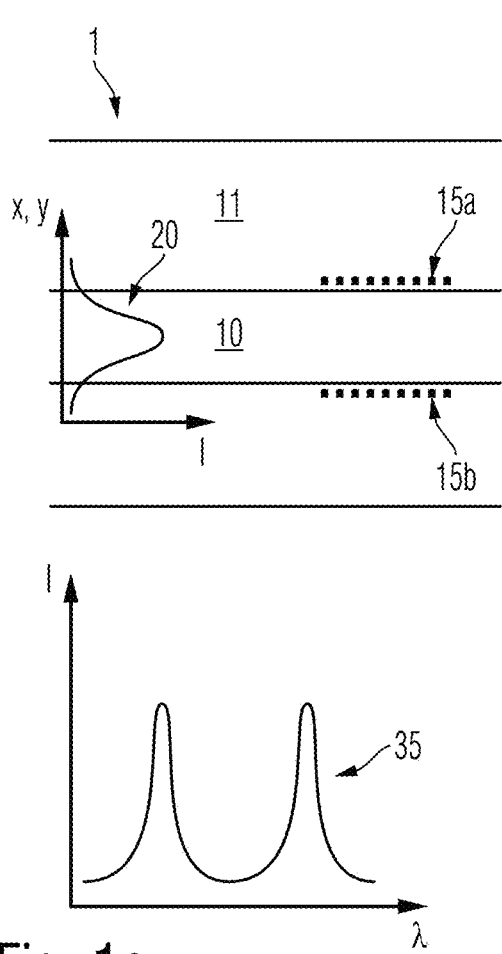
FIGS. 1a and 1b illustrate the measuring principle underlying the invention.

The invention discloses a method for determining the shape of an optical waveguide. The optical waveguide comprises, in a manner known per se, a core and a cladding surrounding the core and having a different refractive index such that light coupled into the core is totally reflected at the interface between the core and the cladding, thus propagating within the core. In some embodiments of the invention, core and cladding can have a polygonal or circular cross-section so that they have the form of an optical waveguide. Depending on the diameter of the core, the optical waveguide according to the invention can be or include a single mode fiber or a multimode fiber. The optical waveguide suggested according to the invention can be or include a glass fiber or a polymer fiber. In other embodiments of the invention, the cladding can be or include a planar substrate, at least one core being arranged within the substrate, for example by inscription with a short pulse laser.

According to the invention, it is further suggested that the optical waveguide comprises a plurality of fiber Bragg gratings. The Bragg gratings each comprise a plurality of spatial regions, or voxels, which have a refractive index that is modified compared to the surrounding region. In some embodiments, the Bragg gratings can be manufactured by inscription with a short-pulse laser. The Bragg gratings can be arranged inside the core and/or in the boundary region between core and cladding or inside the cladding, preferably in the evanescent region of the core. The presence of Bragg gratings has the effect of reflecting light of a predeterminable wavelength that depends on the grating constant of the Bragg grating. Light of other wavelengths, on the other hand, is transmitted. In this respect, the Bragg grating acts as a bandpass filter.

If the grating constant of the Bragg grating changes, for example due to torsion, stretching, or compression of the optical waveguide or due to a changing curvature, the wavelength of the light reflected by the Bragg grating is changed as well. Travel-time measurement and/or wavelength multiplexing can be used to determine the location of the respective Bragg grating within the fiber.

In order to carry out the method according to the invention for determining the shape of the optical waveguide, light from a light source is coupled into the optical waveguide. In some embodiments, the light source can be selected from any of a semiconductor laser and/or a light emitting diode and/or a superluminescent diode. The light source can, in some embodiments of the invention, emit broadband light so that different partial spectra of the light are reflected by different Bragg gratings within the fiber.

The light coupled into the optical waveguide in this way is at least partially reflected within the optical waveguide. On the one hand, the reflection can be effected by the Bragg gratings in the optical waveguide. In other embodiments of the invention, the free end of the optical waveguide which is opposite the light source can be mirrored so that at least some of the coupled-in light is also reflected there.

The reflected light from the optical waveguide is subsequently spectrally analyzed, i.e. the reflected light is supplied to a spectrometer which determines light intensity versus wavelength. In some embodiments of the invention, the spectrometer can, for this purpose, contain at least one micro-optical component as a planar optical filter element. The planar optical filter element can be selected from an arrayed waveguide grating and/or a Mach-Zehnder interferometer and/or a delay line interferometer and/or a directional coupler. This can lead to a robust design of the device according to the invention, which allows a reliable use.

In some embodiments of the invention, a photodiode or a photodiode array or a CMOS sensor or a CCD sensor can be used to determine the light intensity. A photodiode array or a CMOS sensor or a CCD sensor can be designed as an area sensor or a line sensor. These components can be integrated with the micro-optical component in a simple manner.

According to the invention, it is now suggested to analyze the spectrum detected in this way by means of a self-learning neural network and to have it determine the shape of the optical waveguide from the measured spectrum. The neural network here has the advantage that it not only evaluates the intensity and the wavelength of the light reflected by the Bragg gratings, but also uses the intensity and type of the background signal as a further criterion for determining the shape of the optical waveguide. The prerequisite for this is that the neural network has been conditioned by training data, i.e. the self-learning neural network is supplied with known shapes of the optical waveguide and resulting spectra of the reflected light. The self-learning neural network here represents an artificial intelligence which optimizes itself on the basis of this training data and is thus gradually able not only to identify the exact, previously learned shape from the supplied spectrum, but also to reliably identify deviating shapes from deviating spectra by interpolation. A neural network trained in this way can thus also recognize polarization effects or torsion of the optical waveguide which, in the case of known static evaluation algorithms, make the shape determination of the optical waveguide impossible as artifacts. This increases the reliability of the shape identification.

In some embodiments of the invention, the training data can comprise more than 600 or more than 900 or more than 4000 or more than 10000 or more than 100000 data sets. In each case, a data set comprises a measured spectrum and the associated shape of the optical waveguide. The greater the number of training data, the better the artificial intelligence containing the self-learning neural network adapts to the task of shape determination so that the results obtained become correspondingly more accurate in real operation.

In some embodiments of the invention, the training data can be produced in an automated manner using a device which is designed to deform the optical waveguide, detect the shape, and measure the spectrum associated with the particular shape. After detecting the shape of the optical waveguide and the spectrum associated with it, the device can deform, in automated fashion, the waveguide into another shape and then detect its shape and the spectrum associated with it again. In this way, large amounts of training data can be produced in a short time. This training data can comprise torsional stresses of the waveguide in addition to the three-dimensional curvature of the optical waveguide.

In some embodiments of the invention, the deformation of the optical waveguide can be performed by a robot arm. A robot arm of this type is a multifunctional automatic handling machine consisting of a series of rigid links connected to one another by rotary and/or sliding joints. The joints are adjusted by controlled drives. One end of the link chain formed in this way is the base by means of which the robot arm is fixed, for example, on a tabletop or optical bench. The other end is freely movable and equipped with a tool or gripper for picking up a longitudinal portion of the optical waveguide. Thus, by moving the robot arm, the optical waveguide can be brought into a defined shape. The robot arm can be programmed in such a way that it systematically moves the optical waveguide in one, two, or three spatial directions and/or one, two, or three axes of rotation so that a complete set of training data can be obtained for a predefinable case of application.

In some embodiments of the invention, detecting the shape of the optical waveguide can be performed from the position of the robot arm. The position of the robot arm can be either the outputted desired values or the actual values reported back by the robot arm after approaching the respective position. The relative position of the end of the robot arm and a clamping point of the optical waveguide, as well as its length and modulus of elasticity, can then be used to determine which course of curvature the optical waveguide takes in three-dimensional space.

In some embodiments of the invention, the shape of the optical waveguide can be detected by electronic image processing from at least one image of the optical waveguide. In yet another embodiment of the invention, the shape of the optical waveguide can be obtained from both the position of the robot arm and at least one photographic image of the optical waveguide. As a result, both measurements can be made plausible against each other and the accuracy of the shape determination can be increased when producing the training data.

An optical waveguide according to the invention can be provided with a movable component and in this way detect its shape and position in space. A component according to the invention can be selected, for example, from a catheter or an endoscope or a biopsy needle or from a deformable aerodynamic structure, e.g. a sail or a sail batten.

Figure 1B:
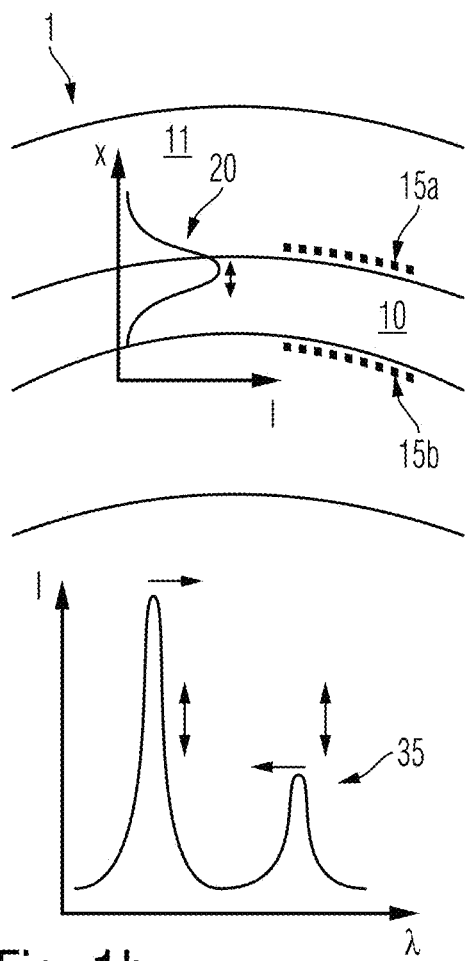

Turning now to the attached drawings, FIG. 1 is used to explain the measuring principle underlying the invention. FIG. 1A illustrates a straight optical waveguide, and FIG. 1B illustrates a curved optical waveguide.

In each case, the optical waveguide 1 has a core 10 and a cladding 11 surrounding the core. For example, the cladding 11 can concentrically surround the core 10. Core and cladding can be made of glass or polymer. Between the core 10 and the cladding 11 there is an interface where light 20 propagating in the core 10 is totally reflected. As a result, the light can be guided in the core 10.

Furthermore, there is at least one Bragg grating 15 in the optical waveguide. In the illustrated exemplary embodiment, two Bragg gratings 15A and 15B are present in the same longitudinal portion of the optical waveguide 1. The Bragg gratings 15 each consist of a plurality of spatial regions, or voxels, which have a refractive index which differs from that of the surrounding material. The spacing of adjacent voxels defines the grating constant. The effect of the Bragg grating 15 is to reflect light of a predeterminable wavelength which is defined by the grating constant. Light of a different wavelength can pass through the Bragg grating 15 in a substantially undisturbed fashion.

The Bragg gratings 15 can be arranged in the core. In the illustrated exemplary embodiment, the Bragg gratings 15 are arranged in the evanescent region of the cladding. The evanescent region is defined by the fact that a portion of the intensity of the light propagating in the core penetrates into it, although the total reflection nominally occurs at the interface.

FIG. 1A further shows an exemplary mode field of light 20, which propagates in the core. The intensity versus the spatial coordinate of the cross-section of the optical waveguide 1 is shown. It is here clear that a portion of the intensity enters the core 11 and can thus interact with the Bragg gratings 15 located in the evanescent region.

FIG. 1B shows that when the optical waveguide 1 is curved, the outer Bragg grating 15A is stretched and the inner Bragg grating 15B is compressed. This can lead to a change in the grating constants, which can be identified by a shift in the intensity maximum of the reflected light. In addition, the mode field 20 shifts relative to the core 10. This results in an increase in the intensity of reflected light in the Bragg grating 15A on the outside of the curvature and a decrease in intensity on the inside.

FIGS. 1A and 1B each show a spectrum 35 that can be measured on a straight waveguide and a curved waveguide. In addition to shifting the position of the reflection maxima and their intensity, the background field between the intensity maxima can also be changed by shifting the mode field 20 of the propagating light.

Figure 2:
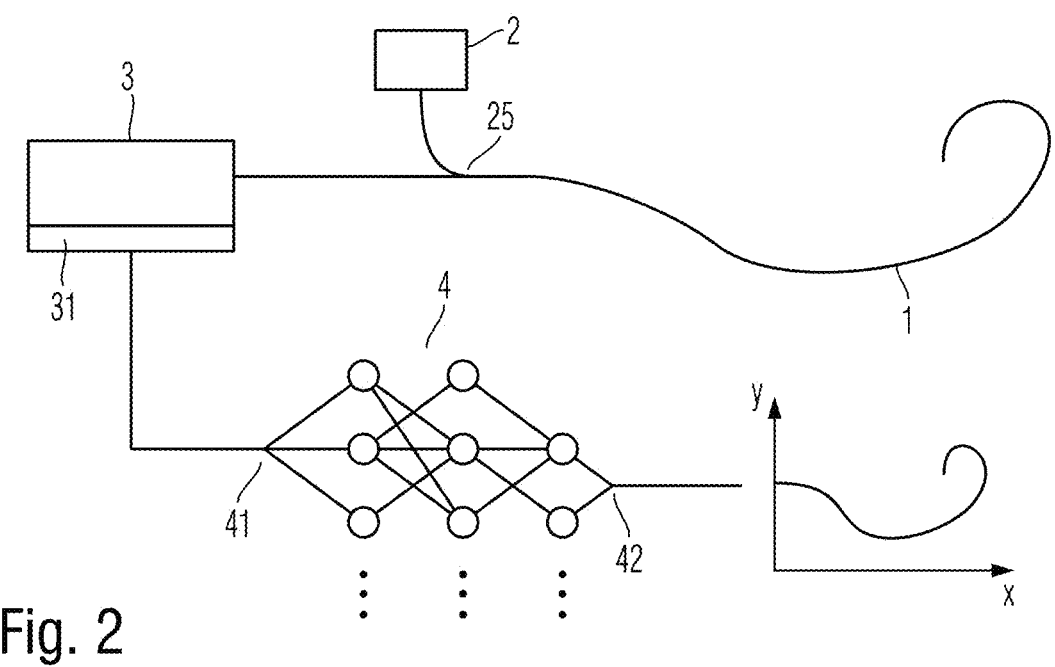
FIG. 2 illustrates a block diagram of a device according to the invention for determining the shape of an optical waveguide.

With reference to FIG. 2, a device for determining the shape of an optical waveguide is explained in more detail. The device according to FIG. 2 shows an optical waveguide 1, which can be attached to a mechanical object, the shape change of which shall be detected. For example, this object can contain or consist of a biopsy needle and/or an endoscope and/or a catheter and/or an aerodynamic profile. For example, an aerodynamic profile can be a sail or a portion of a sail, such as a sail batten. The sail can be laminated from a foil material or woven from a textile material. In this case, the optical waveguide 1 can be glued on or woven in or laminated in. Optionally, such a sail can be stabilized by sail battens. The sail battens, which are made of fiber-reinforced plastic material, for example, can also be equipped with an optical waveguide 1.

The device according to FIG. 2 further contains a light source 2, which can be e.g. a superluminescent diode or a light-emitting diode. The light source 2 can emit broadband radiation covering the Bragg wavelengths defined by the grating constant of the Bragg gratings 15.

The light from the light source 2 is coupled into the optical waveguide 1 via a coupler 25 and propagates in its core 10, as described above. Upon interaction with the Bragg gratings 15, a portion of the propagating light is reflected back in the direction of incidence. In addition, the light can be absorbed, for example by grating defects or imperfections in the structure of the optical waveguide 1. Finally, some of the intensity can enter the cladding 11 and/or leave the optical waveguide 1 by evanescent coupling.

The reflected light modified in this way reaches a spectrometer 3, which can e.g. be designed as integrated micro-optical component. By way of example, a micro-optical component of this type can be designed as an AWG. The spectrometer 3 images light of different wavelengths at different locations where the spectrum can be detected by a spatially resolving detector 31.

The spatially resolving detector 31 can contain, for example, a photodiode array, a CCD sensor or a CMS sensor, or a CMOS sensor. The above mentioned sensors can be designed e.g. as a line sensor or an area sensor.

The electrical signal from the spatially resolving detector 31 can optionally be supplied to an A/D converter and subsequently further processed as a digital signal. This signal representing the spectrum 35 is supplied to a neural network 4 or an artificial intelligence having an input 41 and an output 42.

The neural network 4 contains a plurality of nodes or neurons, which can be organized in an input plane and an output plane and at least one center plane. The neural network 4 is a self-learning neural network or an artificial intelligence, i.e. the connections between individual neurons change during the operation of the neural network 4, so that the quality of the identification increases with an increasing number of training data or longer operation. Data representing the two- or three-dimensional shape of the optical waveguide 1 is then available at the output 42 of the neural network 4. According to the invention, it was identified that, by using the neural network, the shape of the optical waveguide 1 from the spectrum 35 can be determined with greater accuracy. This in particular because the background signal changing with curvature is also used for the plausibility check or determination of the shape and in contrast to known evaluations the shape is not only determined from the position and/or the intensity of the reflection maxima. As a result, the shape of an object connected to the optical waveguide 1 can be determined with greater accuracy.

Figure 3:
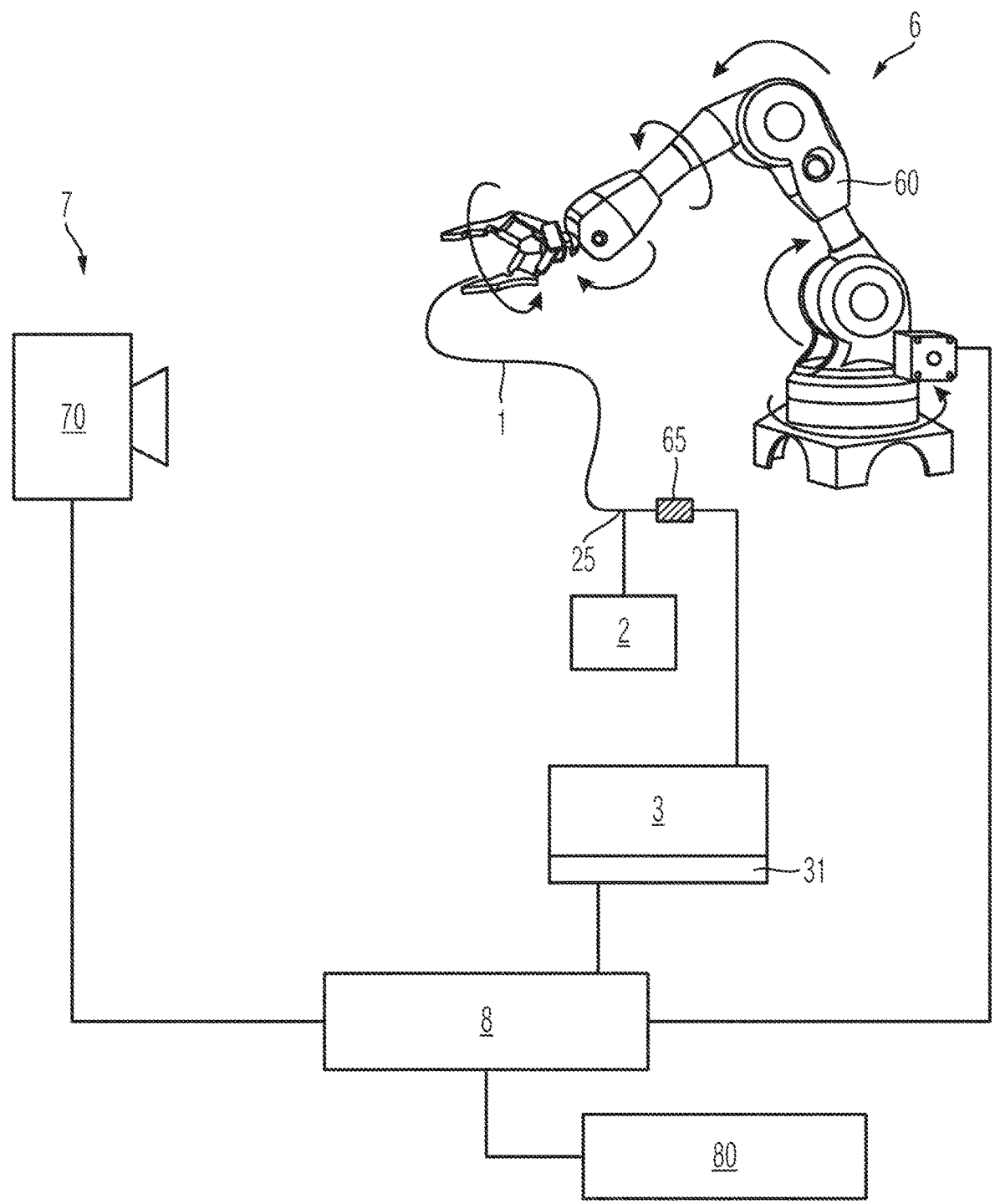
FIG. 3 illustrates a block diagram of a device according to the invention for generating training data.

FIG. 3 shows a device for producing training data for a neural network 4. Since the quality of the shape determination of the optical waveguide 1 is correlated with the quality of the training data, it is advantageous to produce as large a number of training data as possible in a finite time. The device which can be used for this purpose is explained in more detail with reference to FIG. 3. FIG. 3 shows an optical waveguide 1 to which light can be supplied via a coupler 21 from a light source 2, as described above. The light reflected by the optical waveguide 1 is supplied to a spectrometer 3 and a spatially resolving detector 31, as described above. Optionally, an A/D converter can be provided which digitizes the data from the spatially resolving detector 31.

The optical waveguide 1 is held with one end or a longitudinal portion in a clamping point 65. An opposite end or a spaced-apart longitudinal portion is received in an apparatus 6 for deforming the optical waveguide. By means of the apparatus 6 for deforming the optical waveguide, the optical waveguide can be brought into a curved shape deviating from the straight-line course. For this purpose, the apparatus 6 for deformation can have, for example, a robot arm 6. The robot arm is designed to be rotatable and/or pivotable about several axes so that the optical waveguide 1 can be deformed in one, two or three spatial directions and/or in one, two or three directions of rotation.

The shape of the optical waveguide 1 can then be determined by an apparatus 7 for detecting the shape. The apparatus 7 for detecting the shape can include, for example, a digital camera 70 that uses a CCD or CMOS sensor and a lens to produce a digital data stream which represents the shape of the optical waveguide 1.

Alternatively or additionally, the apparatus 7 for detecting the shape can be integrated in the apparatus 6 for deforming the optical waveguide 1, or the shape of the optical waveguide 1 can be determined mathematically from the position of the apparatus 6 for deformation. Next, the detected shape of the optical waveguide is stored in a memory 80 together with the measured spectrum 35. Thereafter, the optical waveguide 1 is changed to a different shape, the shape is detected, and the spectrum of reflected light is measured. This data is also stored in memory 80. Then, this procedure is repeated cyclically. A microprocessor or microcontroller 8 performs the data acquisition as well as the control of the apparatus 7 for detecting the shape as well as the apparatus 6 for deforming the optical waveguide 1 so that different shapes of the optical waveguide can be systematically traversed or a plurality of statistically selected shapes can be detected. In such a manner, it is possible to produce, in some embodiments of the invention, more than 600 or more than 900 or more than 4000 or more than 10000 or more than 100000 data sets, each data set receiving at least one shape of the optical waveguide 1 and a measured spectrum 35. Finally, on the basis of this data, the neural network 4 can be trained so that, unlike a conversion table, it not only assigns a shape to a concretely measured spectrum, but also arrives at a meaningful result if, in real operation, a shape is present which is not identically contained in the training data or a spectrum is detected which is not identically contained in the training data. The neural network 4 used according to the invention allows the reconstruction of the shape also in this case by interpolation or similarity considerations.

Figure 4:
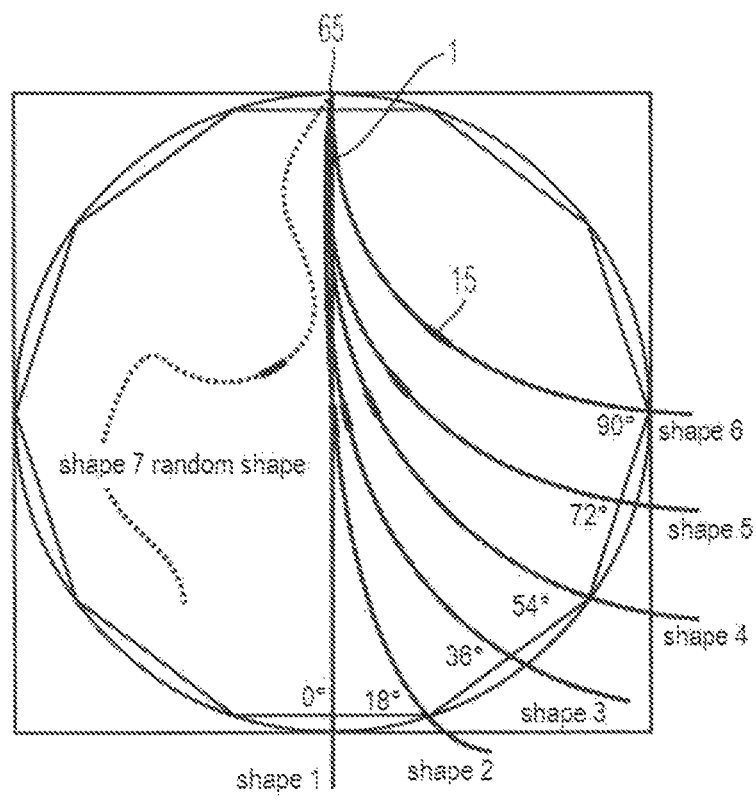
FIG. 4 illustrates different shapes of an optical waveguide.

The invention will be explained in more detail below by means of an exemplary embodiment. FIG. 4 here shows different shapes of an optical waveguide, FIG. 5 shows the respectively associated spectra 35, and FIG. 6 shows the shape reconstruction depending on the quality of the training data.

As explained with reference to FIG. 4, an optical waveguide 1 is considered as an example, which has a clamping point 65. The free end opposite to the clamping point 65 is swiveled once by 0°, then by 18°, 36°, 54°, 72° and 90° within a plane. This results in a curvature of the optical waveguide 1 in one dimension.

Figure 5:
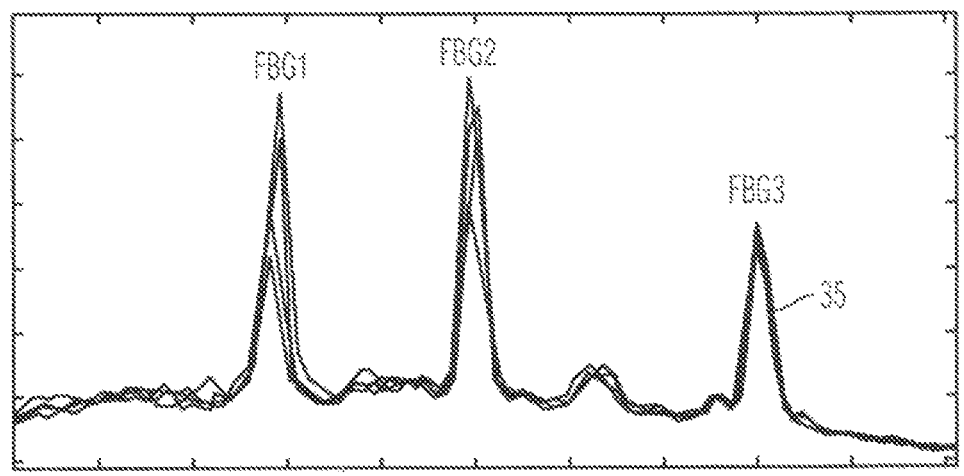
FIG. 5 illustrates the spectra obtained when the shape is changed.
Figure 6:
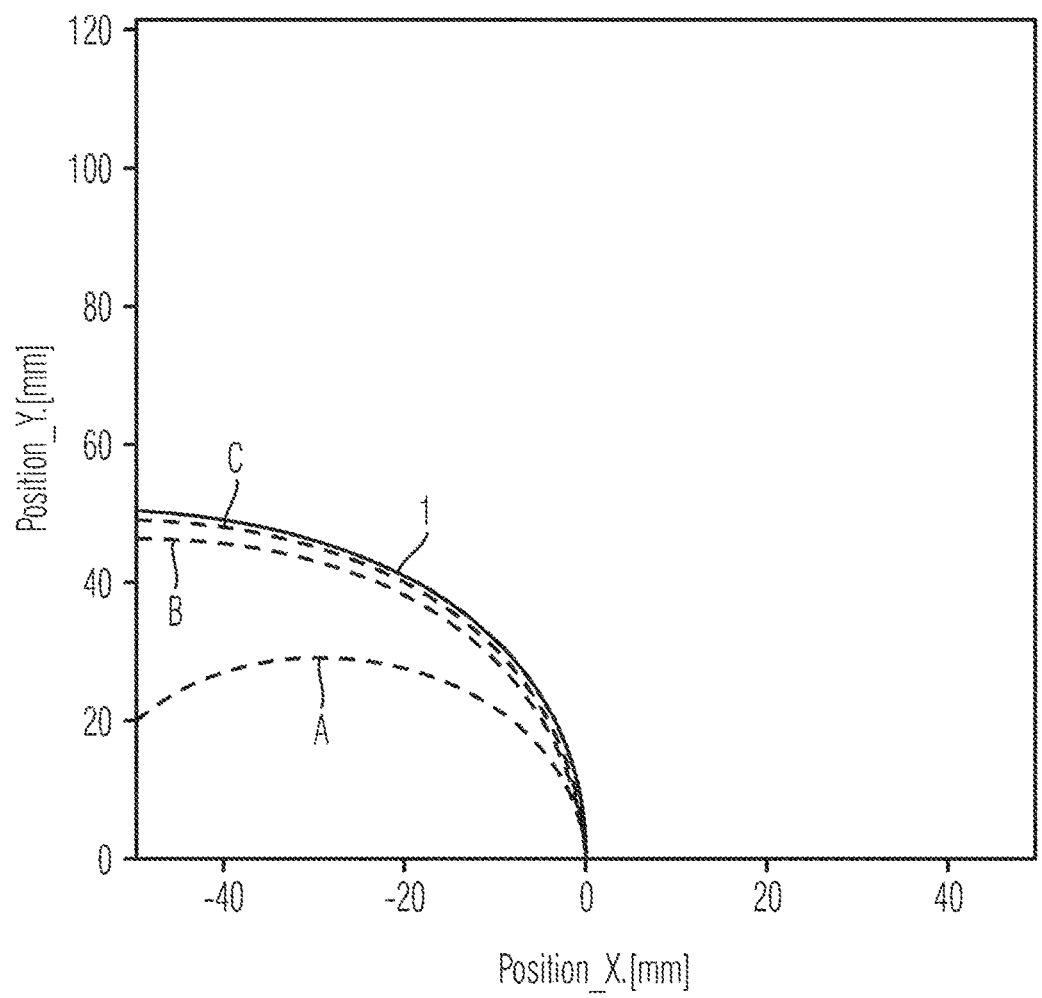
FIG. 6 illustrates the quality of the shape reconstruction on the basis of the amount of training data.

As FIG. 5 shows, the measured spectrum of three fiber Bragg gratings, which are all arranged in a longitudinal portion of the optical waveguide 1, changes for each bending angle or each radius of curvature. Thus, on the one hand, the measured intensity of the reflected light varies in the three reflection wavelengths defined by the grating constant. In addition, however, the background between the intensity maxima also changes.

This data is collected as training data and used to train a neural network as described on the basis of FIG. 2. FIG. 6 shows reconstructed shapes obtained with a setup according to FIG. 2. Here, the position of the optical waveguide in the plane shown in FIG. 4 is plotted on the ordinate or abscissa. Shown is the actual course of the optical waveguide 1. Also shown are measuring curves A, B and C showing the shape of the optical waveguide 1 that is reconstructed by the neural network 4.

FIG. 6 shows that the reconstruction according to curve C follows the actual course of the optical waveguide except for a small measurement error. The deviations of the measured shape from the actual shape are slightly larger in figure B. Figure A shows a considerable deviation, which is useless in practice.

Curves A, B and C were all obtained with the identical device shown in FIG. 2. The difference in each case is the amount of training data used to train the neural network 4. Curve A shows a neural network that was only provided with a single set of data, i.e. only a single spectrum was used that was detected at exactly a single curvature.

Curve B shows the result of a neural network which was trained with 600 data sets. Curve C was obtained with a neural network that was trained with 900 data sets. FIG. 6 shows that already 600 data sets are sufficient to train the neural network in such a way that it meets low accuracy requirements, i.e. produces an error of a few millimeters. When 900 data sets are used, the reconstruction is so accurate that the error is below one millimeter. This comparatively small number of training data can also be obtained in a short time using the device presented according to the invention. In the same way as shown herein for a simple two-dimensional case, the device according to the invention and the method according to the invention can also be used to reconstruct complex shapes in three-dimensional space.

Of course, the invention is not limited to the illustrated embodiments. Therefore, the above description should not be regarded as restrictive but as explanatory. The following claims are to be understood in such a way that a stated feature is present in at least one embodiment of the invention. This does not exclude the presence of further features. If the claims and the above description define "first" and "second" embodiments, this designation is used to distinguish between two similar embodiments without determining a ranking order.

The invention claimed is:

1. A method for determining the shape of an optical waveguide having
  a plurality of fiber Bragg gratings, comprising:
  coupling light of a light source into the optical waveguide,
  coupling the reflected light out of the optical waveguide,
  determining spectrum data of the reflected light by measuring intensity versus wavelength of the reflected light,
  providing the spectrum data to a self-learning neural network having been preconditioned by training data, and
  determining the shape of the optical waveguide by means of said self-learning neural network,
  wherein:
  the training data for preconditioning the self-learning neural network is generated by:
    (a) providing a robot arm configured to hold the optical waveguide;
    (b) moving the robot arm to thereby deform the optical waveguide into a deformed shape;
    (c) measuring spectrum data of reflected light from the deformed optical waveguide;
    (d) storing the measured spectrum data in a memory; and
    (e) repeating steps (b), (c) and (d).

2. The method according to claim 1, wherein:
  the training data comprises a plurality of data sets, each data set comprising measured spectrum data and an associated shape of the optical waveguide.

3. The method according to claim 2, wherein:
the training data contains more than 600 data sets.

4. The method according to claim 1, comprising:
detecting the shape of the optical waveguide from any position of the robot arm, by electronic image processing of at least one image of the optical waveguide.

5. The method according to claim 1, comprising:
attaching the optical waveguide to one from the group consisting of: a catheter, an endoscope, a biopsy needle and a deformable aerodynamic structure, prior to determining the shape of said optical waveguide.

6. The method according to claim 1, wherein the shape of said optical waveguide comprises any of its curvature and its torsion.

7. The method according to claim 1, wherein:
the training data comprises at least 10,000 data sets, each data set comprising measured spectrum data and an associated shape of the optical waveguide.

8. A device for determining the shape of an optical waveguide, comprising
at least one optical waveguide having a plurality of fiber Bragg gratings,
at least one light source adapted to couple light into the optical waveguide,
at least one spectrometer adapted to determine spectrum data of the light reflected in the optical waveguide by measuring intensity versus wavelength of the reflected light,
wherein:
the device further comprises a microprocessor which comprises a self-learning neural network having been preconditioned by training data and having at least one input and at least one output, the input being configured to receive said spectrum data and the output being configured to provide data representing the shape of the optical waveguide, and
the training data comprises measured spectrum data of light previously reflected in a deformed optical waveguide held by a robot arm programmed to systematically move the optical waveguide into different shapes.

9. The device according to claim 8, wherein:
the training data comprises at least 10,000 data sets, each data set comprising measured spectrum data and an associated shape of the optical waveguide.

10. The device according to claim 8, wherein:
said self-learning neural network has been preconditioned with training data comprising of a plurality of data sets, each data set comprising measured spectrum data and an associated shape of the optical waveguide.

11. A device for generating training data for a neural network, comprising:
at least one optical waveguide having a plurality of fiber Bragg gratings,
at least one light source configured to couple light into the optical waveguide,
at least one spectrometer configured to determine spectrum data of the light reflected in the optical waveguide by measuring intensity versus wavelength of the reflected light,
a robot arm configured to hold the optical waveguide and programmed to move the optical waveguide to thereby deform the optical waveguide,
an apparatus configured to detect the shape of the deformed optical waveguide, and
a memory configured to store data representing the shape of the optical waveguide and the spectrum data.

12. The device according to claim 11, wherein:
the data stored in the memory comprises at least 10,000 data sets, each data set comprising measured spectrum data and an associated shape of the optical waveguide.

13. The device according to claim 11, wherein:
the apparatus configured to detect the shape of the optical waveguide is configured to detect a position of the robot arm.

14. The device according to claim 11, wherein:
the apparatus configured to detect the shape of the optical waveguide comprises a camera configured to produce a data stream representing an image of the optical waveguide.

* * * * *